United States Patent [19]

Rodler

[11] 4,401,121

[45] Aug. 30, 1983

[54] DEVICE FOR TREATMENT WITH INTERFERENCE CURRENTS

[75] Inventor: Hans Rodler, Graz-Neuhart, Austria

[73] Assignee: Firma Somartec S.A., Geneva, Switzerland

[21] Appl. No.: 231,921

[22] Filed: Feb. 5, 1981

Related U.S. Application Data

[62] Division of Ser. No. 3,961, Jan. 16, 1979, Pat. No. 4,280,504.

[51] Int. Cl.³ ............................................. A61N 1/36
[52] U.S. Cl. ............................. 128/420 A; 128/422
[58] Field of Search ........... 128/420 A, 420 R, 419 R, 128/421, 422, 423 R

[56] References Cited

U.S. PATENT DOCUMENTS

| | | | |
|---|---|---|---|
| 3,774,620 | 11/1973 | Hansjurgens | 128/420 A |
| 3,794,022 | 2/1974 | Nawracaj et al. | 128/420 A |
| 3,893,463 | 7/1975 | Williams | 128/421 |
| 3,895,639 | 7/1975 | Rodler | 128/420 A |
| 3,918,461 | 11/1975 | Cooper | 128/420 A |
| 4,071,038 | 1/1978 | Nawracaj et al. | 128/420 A |

FOREIGN PATENT DOCUMENTS

| | | | |
|---|---|---|---|
| 2159437 | 4/1973 | Fed. Rep. of Germany | 128/420 |
| 2242996 | 4/1975 | France | 128/422 |

Primary Examiner—Lee S. Cohen
Attorney, Agent, or Firm—Antonelli, Terry & Wands

[57] ABSTRACT

In interference current therapy, medium-frequency alternating currents are applied by means of electrodes to the body of a patient that is to be treated, the currents differing by a low-frequency difference frequency and interfering with each other in the area under treatment with development of a low frequency beat signal that can effect stimulation. Especially in the case of low frequencies, precise control of the frequency interference current is difficult, and at least one of the medium frequencies must be variable, for adjustment of the low frequency. According to the invention, a common oscillator is provided for both medium frequencies, the essentially higher frequency output of which is divided by a programmable divider into two or more frequencies that differ by the required amount, whereby at least one of the dividers is variable. Various schemes are described for execution of variable frequency division.

7 Claims, 5 Drawing Figures

DEVICE FOR TREATMENT WITH INTERFERENCE CURRENTS

This is a division of U.S. application Ser. No. 003,961, filed Jan. 16, 1979, now U.S. Pat. No. 4,280,504.

FIELD OF THE INVENTION

The present invention relates to a device for treatment with interference currents, where two or more frequencies with a slight difference in frequency interfere with one another in the body that is to be treated.

BACKGROUND OF THE INVENTION

In interference current therapy, an electromedical treatment process is employed in which, in the area of treatment in question, a stimulus is developed with a low-frequency electric current. The immediate use of low-frequency alternating current of sufficient current intensity runs into difficulties however, because the electrical resistance of the area of treatment is relatively high at low frequencies. Because of this high resistance, there are disagreeable stimulations of the skin in the region of attachment of the electrodes when using low frequency signals, because of the necessary high voltage, and the intensities of stimulation deep within the treatment area are inadequate.

Therefore, in interference current therapy, two (or more) medium-frequency currents (with a frequency for example of a few thousand Hertz) that are independent of each other are applied by means of electrodes placed on the skin. These medium-frequency currents, which are respectively ineffective for stimulation, present frequencies that differ by a low-frequency difference. These medium-frequency currents penetrate into the depth of the area of treatment so as to interfere with each other and thereby produce a low-frequency beat that corresponds to the frequency difference. This low beat frequency, because of the physiological properties of the nerves, is stimulating.

In known arrangements of this kind (see German Pat. No. 1,764,672), use is made of two frequencies of about 5000 Hz, where one differs slightly from the other, e.g. 5000 Hz and 5001 Hz. The great difficulty in this arrangement resides in the fact that this slight difference in frequency is very difficult to maintain, and also that one of the two frequencies has to be variable.

SUMMARY OF THE INVENTION

The present invention, therefore, is directed to the problem of creating a device capable of stable maintenance of the frequency difference within a tolerance of 0.01% between the two frequencies, since it is particularly low differences that are thereapeutically valuable.

According to the invention, this is achieved by the use of a common oscillator, the output of which is divided from a substantially higher frequency, by programmable dividers, into two or more frequencies that differ by the required amount, whereby at least one of the dividers is variable.

According to the invention, the variable division can also be attained by extending the output period of the frequency dividers by blocking individual timing pulses, or several such pulses, per output period, whereby the number of blocked pulses will be determined by a supplementary switchable counter or monostable flip-flop which, advantageously, is automatic.

According to the invention, the variation of frequency division can also occur through the introduction of additional pulses to the input pulses, as a function of the output pulses, whereby the number of introduced pulses is controlled by a monostable multivibrator with adjustable pulse width, advantageously by a supplementary counter, whereby the additional pulses are phase shifted with respect to the input frequency pulses, so that they are introduced in between pulses and shorten the duration of the output period.

In the device according to the invention, two different frequencies are produced digitally, by division. Since at least one of the dividers can be variably programmed, arbitrary differences of frequency can be established. The minimum settable difference here depends upon the magnitude of the control frequency. Thus, for example, with a control frequency of 50 MHz and a 1/10,000 frequency division (and hence a divided frequency of 5000 Hz) the minimum obtainable frequency difference is 0.5 Hz. By re-programming the divider, frequency differences of 1 Hz, 2 Hz, 4 Hz, 6 Hz etc. can be obtained. Since these frequency differences are not only to be stably set but also automatically varied in a specific rhythm, according to the invention another frequency divider is connected after the divider output, and the output of this additional frequency divider varies the program inputs of the variable divider via a switch and a counter device. By these arrangements, different frequencies in any sequence can automatically be brought into interference with each other on the body. Therefore, it is possible not only to have fixed settable frequencies, but also programs that run automatically with this device.

In frequency dividers in which the pulse-pause ratios are not 1:1, it is advantageous to connect, thereafter, a pulse shaping stage that produces a symmetrical square wave from the divided pulses.

Since sinusoidal current wave forms are usable in treatment with interference frequencies, the pulse shaping stage according to the invention is followed by a curve transforming element which produces a sinusoidal curve from the square wave.

This arrangement has a number of advantages as compared with existing devices.

Thus, the pulse-pause ratio and the pulse frequency of the oscillator fixes the frequency difference so that no supplementary servicing or tuning operation is necessary. The interference frequency thus does not depend upon temperature differences, voltage fluctuations or other factors, so that a simple and inexpensive construction is produced. An economic advantage is the simple construction from integrated modules, so that it is possible to build it not only economically but also in a small manageable size. Finally, the digital nature of the device makes possible the use of sensor switches and timing switch devices and full automation of the interference current device.

The invention is discussed in more detail with reference to an example of embodiment, where further features of the invention are described.

DETAILED DESCRIPTION OF THE INVENTION

Figure 1:
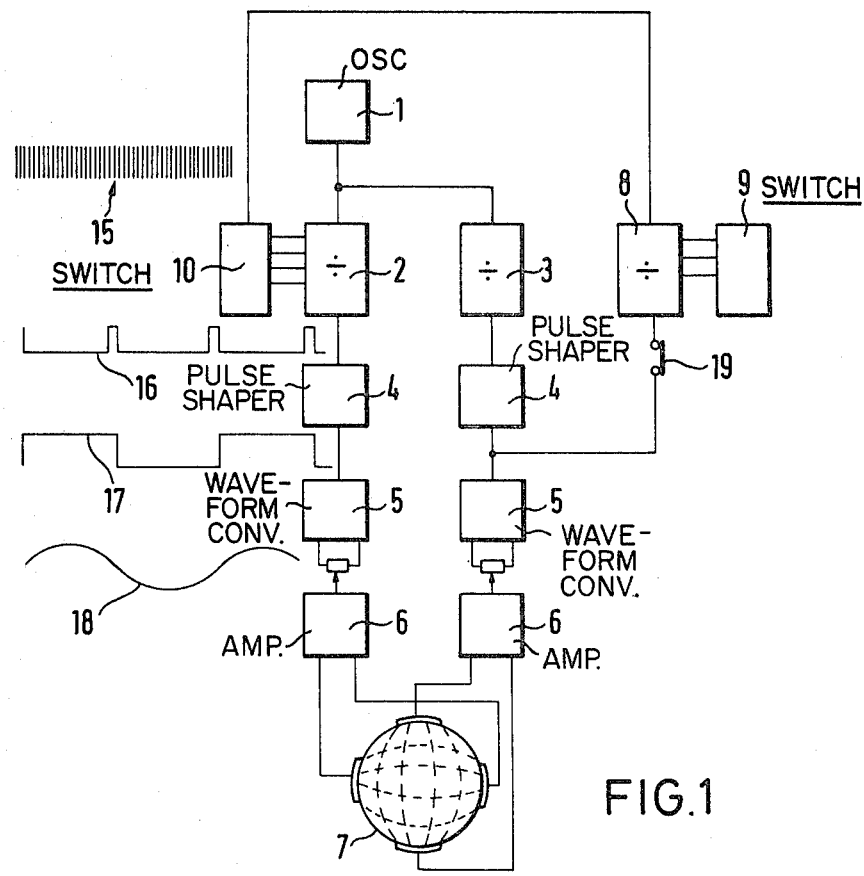
FIG. 1 shows a block diagram of the invention with an appurtenant pulse waveform.

FIG. 1 shows a common oscillator 1 which produces a pulse train 15 and supplies the train 15 to a fixed divider 3 and a programmable divider 2. Using a decadic divider, there are produced narrow output pulses 16 that are converted in pulse shaper stage 4 into a symmetrical square wave 17. Shaping stage 5 converts the square wave 17 into a sinusoidal wave 18. For this purpose, stage 5 may comprise a fundamental wave filter. Output amplifiers 6 supply the part currents to patient 7 via two separate circuits so that interference frequencies are generated in the patient's body. An additional divider 8 which can be controlled by a switching device 9 sets the fixedly adjusted part-frequency at a frequency of 1 Hz per second and increments the contents of control register 10 of the variable counter every second, so that the interference frequency is automatically increased each second.

This automatic device can be cut off by means of switch 19, so that switching device 10 can also be arbitrarily varied. This arrangement thus delivers fixed adjustable interference frequencies, but also interference phenomena that run automatically, corresponding to the interference current method in present-day practice.

Figure 2:
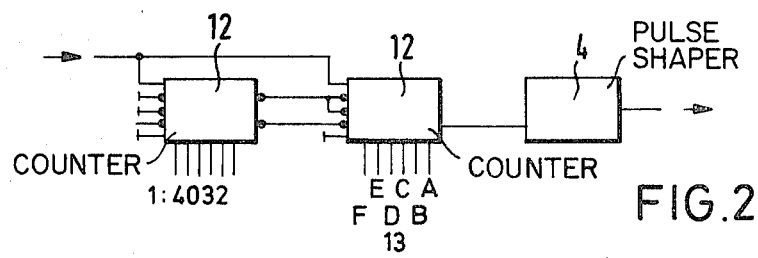
FIG. 2 shows a device with a programmable frequency divider stage.

FIG. 2 shows the circuitry of a programmable divider made of two counter modules 12. Such a frequency divider circuit can change its ratio of division from 1:4096 to 4095:4096. The counter modules 12 are commercially available switching circuits that require no additional wiring.

Figure 3:
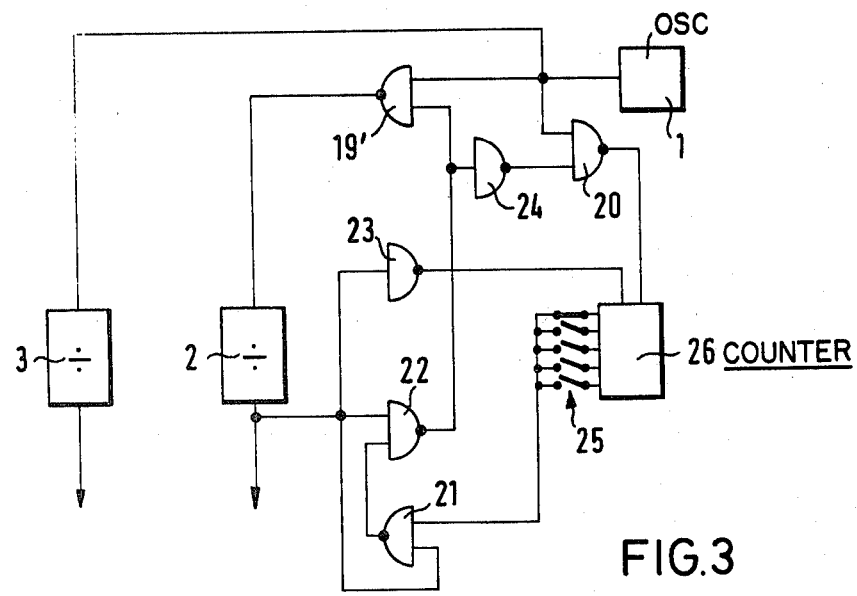
FIG. 3 shows a device in which, by blocking individual pulses, the frequency of one part-frequency can be varied.

Another possibility for changing the frequency division is shown in FIG. 3. Oscillator 1 produces a 25 MHz square wave which is coupled to binary frequency divider 2 via the NAND gate 19' until the output of frequency divider 2 switches from zero to one. At this time, the output of NAND gate 22 goes from one to zero, to disable NAND gate 19' and cut off the input to frequency divider 2. The transition of the output of frequency divider 2 to a "one" also sets the reset input of counter 26 from "one" to "zero," via inverter 23, and also sets the input of NAND gate 21 to "one" and thus enables NAND gate 21. Furthermore, because of the zero at the output of NAND gate 22, NAND gate 20 becomes enabled via inverter 24 and thereby controls counter 26 until the output of this counter switches from zero to one. This has the effect that the NAND gate 21 goes from one to zero and NAND gate 22 also switches from zero to one and blocks NAND gate 20 via inverter 24, so that the output to counter 26 is cut off. At the same time, NAND gate 19' is enabled and frequency divider 2 continues to count pulses. When the output of frequency divider 2 switches to zero upon recycling at the division count, the reset input of counter 26 will be set to one, via inverter 23, with the effect that counter 26 will return to zero and the output will remain at zero.

In this way, NAND gate 21 is set at one, and NAND gate 22 is enabled at the next change from zero to one of frequency divider 2. This frequency divider circuit has the effect, that, by leaving out a single pulse or a plurality of pulses per output period, the output period can be extended. The number of excluded pulses, and hence the length of the output period is controlled by counter 26 whose outputs are selectively connected to NAND gate 21 by a switch 25, depending upon the extension desired.

The omission of a pulse at a 25 MHz frequency and with a 1/5000 division yields a frequency change on the output of frequency divider 2 of 5000 or 4999 Hz. This corresponds to a frequency difference between dividers 3 and 2 and hence an interference frequency of 1 Hz.

Figure 4:
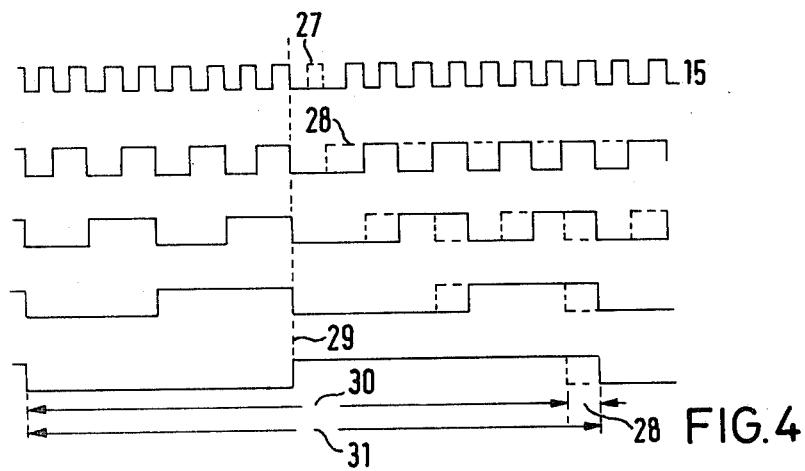
FIG. 4 shows a pulse diagram for FIG. 4.

FIG. 4 shows a pulse diagram in simplified representation, for 1/16 division. The same principle obtains for 1/5000 division. Numeral 15 represents the train of pulses for which upon switchover of the output at 29 from zero to one, the next pulse 27 will be blocked. This results in the omission as at 28 of a timing period for all following divider stages and thereby an extension of the output period from 30 to 31, whereby, in this case, the divider ratio will be increased from 16 to 17.

Figure 5:
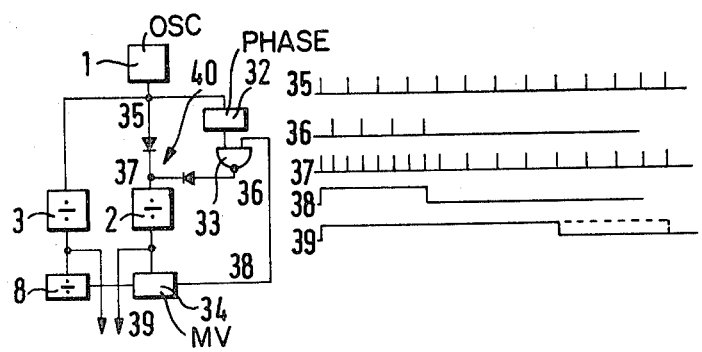
FIG. 5 shows a device in which, by the introduction of phase-shifted pulses, the frequency of one part-circuit can be varied.

In FIG. 5, numeral 1 is a 25 MHz oscillator, the output 35 of which is supplied, on the one hand, to the fixedly set divider 3, and, on the other hand, via diode mixing circuit 40 to variable frequency divider 2, and also to phase changer 32. In phase changer 32 the phase position of the input pulses is changed in such a way that pulses 36 shifted via NAND gate 33 and diode mixing circuit 40 to the input of frequency divider 2 lie between pulses coming directly from oscillator 1 (curve 36).

The output of the variable frequency divider 2 controls monostable multivibrator 34, whose pulse width 38 is controlled automatically or by switching. During the pulse duration 38 of the output of multivibrator 34, NAND gate 33 is conductive and the diode mixing circuit 40 combines pulses 35 with the phase-shifted pulses 36. Thus, frequency divider 2 counts at a 50 MHz rate during pulse 38 and thereby shortens the output period 39. With an introduction of an individual pulse, there is an increase in frequency at a 1/5000 division, from 5000 and 5005. From this it results that the minimum interference frequency is 0.5 Hz. A control voltage for the automatic control of multivibrator 34 can be obtained by a supplementary frequency divider 8 which is connected to the output of the fixedly set frequency divider 3. This control voltage varies the pulse width of the monostable multivibrator 34, e.g. by integration of the frequency appearing at the output of frequency divider 8 (not shown in the illustration). By this integration there is formed a delta voltage that can be utilized for pulse width modulation of a monostable multivibrator.

Pursuant to the invention, the control of the monostable multivibrator or of the counter, for variation of frequency, can be effected for parameters other than those described, e.g. delta voltages, square wave voltages, or waveforms produced by linear structural elements, whereby, in each of the examples, the counting and switchover device can operate via a "one shot" or monostable multivibrator or another switching unit that is capable of delivering signals of controllable pulse width.

While I have shown and described several embodiments in accordance with the present invention, it is understood that the same is not limited thereto but is susceptible of numerous changes and modifications as known to those skilled in the art and I therefore do not wish to be limited to the details shown and described herein but intend to cover all such changes and modifications as are encompassed by the scope of the appended claims.

I claim:

1. In a device for providing electromedical treatment by causing a plurality of signals to be applied by electrode means to a body, said signals being of relatively different frequencies to interfere with one another in the body to be treated, including first means for generating a first relatively high frequency signal in the form of a pulse train; and second means, coupled to said first means and providing an output to said electrode means, for dividing said relatively high frequency signal into a plurality of relatively lower frequency signals that differ in frequency by a difference frequency, the improvement comprising:

means for controllably varying the division of said relatively high frequency signal to one of said relatively lower frequency signals, including means for selectively adding one or more pulses to the pulse train of said relatively high frequency signal and causing the resulting pulse sequence to be controllably divided to a lower frequency signal.

2. The improvement according to claim 1, wherein said adding means includes means for shifting the phase of the pulses of said high frequency signal and inserting selected ones of the phase shifted pulses into said high frequency signal to thereby obtain said resulting pulse sequence.

3. The improvement according to claim 2, wherein said adding means includes a monostable multivibrator, the unstable state of which is controllably variable, and a gating circuit enabled by said monostable multivibrator and coupled between the output of said phase shifting means and a pulse divider circuit.

4. The improvement according to claim 3, further comprising means for converting said one lower frequency signal to a lower frequency sinusoidal wave.

5. The improvement according to claim 1, further comprising means for converting said one lower frequency signal to a sinusoidal waveform.

6. In a device for providing electromedical treatment by causing a plurality of signals to be applied by electrode means to a body, said signals being of relatively different frequencies to interfere with one another in the body to be treated, including first means for generating a first relatively high frequency signal in the form of a pulse train; and second means coupled to said first means and providing an output to said electrode means for dividing said relatively high frequency signal into a first relatively lower frequency signal; the improvement comprising:

third means coupled to said first means for dividing said relatively high frequency signal into a second relatively lower frequency signal which differs in frequency from said first relatively lower frequency signal by a frequency difference, including means for adding one or more pulses to the pulse train of said relatively high frequency signal to produce a higher frequency signal and means for dividing said higher frequency signal to produce said second relatively lower frequency signal.

7. The improvement according to claim 6, further including means for converting said first and second relatively lower frequency pulse signals to a sinusoidal waveform.

* * * * *